United States Patent [19]

Wakselman et al.

[11] Patent Number: 5,138,035
[45] Date of Patent: Aug. 11, 1992

[54] CYCLOPEPTIDE DERIVATIVES USABLE AS SELECTIVE INHIBITORS WITH RESPECT TO PROTEASES WITH ACTIVE SERINE

[75] Inventors: Michel Wakselman, Paris; Jean-Paul Mazaleyrate, Choisy-Le-Roi; Michele Reboud-Ravaux, Paris, all of France

[73] Assignee: Centre National De La Recherche Scientifique, Paris, France

[21] Appl. No.: 477,820

[22] Filed: Jun. 1, 1990

[30] Foreign Application Priority Data

Sep. 2, 1988 [FR] France ................................. 88 11528

[51] Int. Cl.$^5$ ........................ C07K 5/12; A61K 37/00
[52] U.S. Cl. .................................................... 530/317
[58] Field of Search ........................... 530/317; 514/9

[56] References Cited

FOREIGN PATENT DOCUMENTS 0357510  3/1990  European Pat. Off. .

OTHER PUBLICATIONS

Wakselmann et al., Chemical Abstracts, vol. 113, 1990 p. 721, Abst. No. 132827m.
Connert et al., Chem. Abst. vol. 114, 1990, Abst. No. 77553n.
Mor et al., Thrombosis Research, supplement VIII, 1988. pp. 35–44.
Chemical Abstracts, vol. 111, No. 11 Sep. 11, 1989, J. P. Mazaleyrat et al: "Directed enzymic hydrolysis of cyclopeptides containing an aminobenzoic acid residue", p. 319.
Chemical Abstract, vol. 109, No. 3, Jul. 18, 1988, J. P. Mazaleyrate et al.: "Synthesis and enzymic hydrolysis of cyclic peptides containing an anthranilic acid residue", p. 662.
Chemical Abstracts, vol. 109, No. 17, Oct. 24, 1988, M. Reboud-Ravaux et al: "Structural factors in the enzymic hydrolysis of cyclopeptides containing an o–or m–aminobenzoic acid residue", p. 320.
Chemical Abstracts, vol. 110, No. 5, Jan. 30, 1989, A. Mor et al.: "Susceptibility of plasminogen activators to suicide inactivation", p. 259.

Primary Examiner—Merrell C. Cashion, Jr.
Assistant Examiner—A. M. Davenport
Attorney, Agent, or Firm—Oblon, Spivak, McClelland, Maier & Neustadt

[57] ABSTRACT

The invention relates to cyclopeptide derivative usable as protease inhibitors and complying with formula:

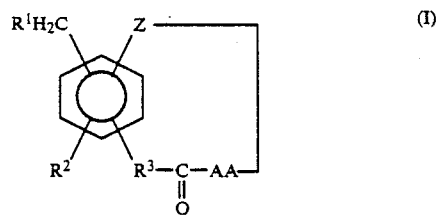

in which $R^1$ is a halogen atom, e.g. bromine or a radical such as $S^+R_2^4X_{1/\nu}^{\nu-}$, $R^2$ is a hydrogen atom, an alkyl radical, a halogen atom or other groups, $R^3$ is NH, O or S, Z comprises a peptide sequence $Z^1$ and a group such that CO has one end connected to the aromatic nucleus and CO-AA is a radical derived fropm an amino acid having a specificity with respect to the protease to be inhibited.

12 Claims, No Drawings

CYCLOPEPTIDE DERIVATIVES USABLE AS SELECTIVE INHIBITORS WITH RESPECT TO PROTEASES WITH ACTIVE SERINE

The present invention relates to novel cyclopeptide derivatives usable as protease inhibitors.

It more particularly applies to proteases with active cysteine or serine such as factors IXa, Xa, XIa, XIIa and VIIa of the coagulation of blood, thrombin, kallikrein of the plasma, activated protein C, activation factors Clr, Cls, D and B in complement, $C_3$ convertase, trypsin, chymotrypsin, elastase, enterokinase, plasmin, activators of plasminogen (urokinase, tpA), acrosine, cathepsin G, chymases, tryptases and proteases dependent on ATP.

More specifically, it relates to novel cyclopeptide derivatives liable to act selectively as inhibitors with respect to a given protease.

It is known that active cysteine or serine proteases are involved in numerous physiological processes. Pathological states can occur when there is a non-equilibrium between a protease and its natural macromolecular inhibitors. In order to obviate this non-equilibrium, synthetic inhibitors could be used and would therefore have a great interest in therapeutics, e.g. in the following pathologies:

- pulmonary emphysema, rheumatoid arthritis, cutaneous aging and inflammation, where the active protease is leucocytic elastase, cathepsin G also being involved;
- tumor invasion and metastasis linked with the presence of proteases such as activators of plasminogen or plasmin;
- antithrombotic action and the prevention of cerebral and coronary infarctions, where the responsible protease is thrombin;
- control of thrombolysis and fertility, relating to the activators of plasminogen and plasmin;
- control of parasites and viruses, because certain viruses produce active cysteine proteases.

For some years research has been carried out with the aim of synthesizing irreversible inhibitors of proteases. Among these are in particular known synthetic inhibitors in the form of derivatives of coumarins, such as 3,4-dihydro-3,4-dibromo-6-bromomethyl coumarin, which is a very effective, irreversible inactivator or inhibitor with respect to cysteine and serine proteases, but which unfortunately lacks selectivity. These coumarin derivatives are in particular described in the book "Proteinase inhibitors" by A. J. Barret and G. Salvesen, Elsevier, 1986, pp. 119-121.

It would also be of great interest to synthesize other inhibitors of proteases, which are specific with respect to a given protease and which make it possible to inactivate the latter without acting on analogous proteases.

The present invention specifically relates to a novel cyclopeptide derivative making it possible to achieve this result.

According to the invention, the cyclopeptide derivative corresponds to the formula:

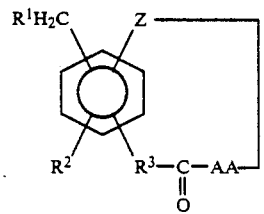

in which:

$R^1$ is chosen from among chlorine, fluorine, bromine and iodine atoms and the radicals $OSO_2R^4$, $OP(O)R^4{}_2$, $OC(O)R^4$ and $S^+R^4{}_2X_{1/\nu}{}^\nu{}^-$ with $R^4$ representing an alkyl, perfluoroalkyl or aryl radical, in which the $R^4$ can be different and $X^-$ represents an anion of valency v;

$R^2$ is a hydrogen atom, an alkyl radical, a halogen atom, $NO_2$, $COOR^5$, $CF_3$, CN or $SO_2R^5$ with $R^5$ representing an alkyl or aryl radical;

$R^3$ stands for an oxygen atom, a sulphur atom or —NH—;

Z comprises a peptide sequence $Z_1$ of amino acids or identical or different analogs and a group chosen from among $-(CH_2)_n-$, $-O(CH_2)_n-$ or CO— at its end connected to the aromatic nucleus with n being an integer from 1 to 8;

a radical derived from an amino acid or an amino acid analog of formula:

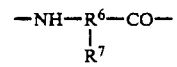

in which $R^6$ represents —N— or —CH— and $R^7$ represents a radical chosen from among H, —CH$_3$, —CH$_2$CH(CH$_3$)$_2$;

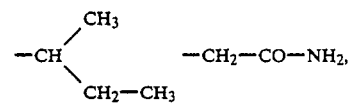

$CH_2-CH_2-COOH$, $-CH_2-CH_2-CO-NH_2-$, $(CH_2)_4-NH_2$, $-CH_2OH$, $-CH_2-SH$

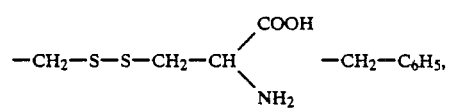

$-CH_2-C_6H_4OH$, $-(CH_2)_3NHC(=NH)-NH_2$, $-CH_2-COOH$, $-CHOH-CH_3$

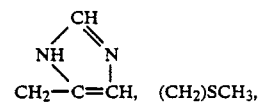

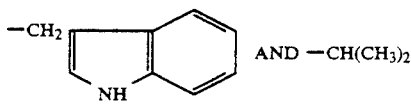 AND —CH(CH$_3$)$_2$ or of formula:

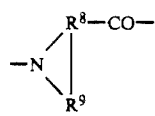

in which R$^8$ represents N or CH and R$^9$ represents the radical —(CH$_2$)$_3$— or —CH$_2$—CHOH—CH$_2$.

The invention also relates to addition salts to pharmaceutically acceptable acids of the cyclopeptide derivatives. For example, it is possible to use such salts when R$^7$ comprises an amino group NH$_2$. The pharmaceutically acceptable acids can e.g. be HCl, HBr, PO$_4$H$_3$, R$^4$COOH, SO$_4$H$_2$, R$^4$SO$_3$H with R$^4$ having the meaning given hereinbefore.

In this formula, the alkyl radicals used generally have 1 to 5 carbon atoms and can be straight or branched. The aryl radicals can have 6 to 14 carbon atoms. Examples of such radicals are methyl, ethyl, phenyl and naphthyl radicals.

In the cyclopeptide derivative according to the invention, the group CH$_2$R$^1$ makes it possible to inactivate the protease and the choice of the peptide sequence Z$_1$, as well as the amino acid C(O)—AA makes it possible to give the desired selectivity with respect to a given protease. Preferably, the peptide sequence Z$_1$ comprises 2 to 8 amino acids or amino acid analogs, which can be the same or different.

The amino acids and amino acid analogs which can be used are e.g. those complying with the formula

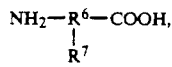

in which R$^6$ and R$^7$ have the meanings given hereinbefore.

Preferably, in the invention, R$^3$ is in the ortho or meta position with respect to Z and in the ortho or para position with respect to R$^1$H$_2$C. Thus, this arrangement makes it possible to obtain the best results with regards to the capacity of the group CH$_2$R$^1$ to inactivate the protease and the capacity of the cyclopeptide chain to selectively adapt to the protease to be inactivated.

The inactivation mechanism firstly corresponds to a cleaving of the cyclopeptide between R$^3$ and the amino acid C(O)—AA, which permits a fixing of the cyclopeptide to the active serine of the protease by the group C(O)—AA, whilst thus forming an acyl enzyme. This cyclopeptide cleaving gives R$^1$ an increased mobility by the formation of an intermediate derivative of the methylene quinonimine type, when R$^3$ represents NH, which is then transformed into methylene aniline with fixing to an amino acid residue of the active site of the enzyme by the methylene group, which thus ensures an inactivation of the enzyme.

Preferably R$^1$ is Cl, Br, OSO$_2$R$^4$ or preferably S$^+$R$_4^2$X$_{1/\nu}^{\nu-}$. X$^-$ can be an anion derived from a pharmaceutically acceptable acid such as Cl$^-$, ClO$_4^-$, Br$^-$, BF$_4^-$, PF$_6^-$, R$^4$COO$^-$, R$^4$SO$_3$ with R$^4$ having the meaning given hereinbefore, e.g. CF$_3$COO$^-$. In S$^+$R$_4^2$X$_{1/\nu}^{\nu-}$, the two R$^4$ can be the same or different and are preferably alkyl or aryl radicals.

In the cyclopeptide according to the invention, Z and AAC(O) are chosen as a function of the protease to be inactivated.

—AA—C(O)— is derived from an amino acid, which corresponds to the primary specificity of the targeted protease class.

In the case where it is wished to inactivate a protease of the chymotrypsin type, —AA—C(O)— is preferably derived from phenyl alanine, tyrosine, tryptophan or methionine and corresponds to the formula:

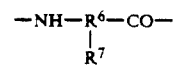

in which R$^6$ is CH and R$^7$ is CH$_2$—C$_6$H$_5$, CH$_2$—C$_6$H$_4$OH,

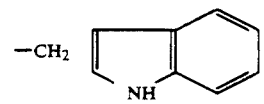

or (CH$_2$)$_2$SCH$_3$.

In the case where the protease to be inhibited belongs to the trypsin group, —AA—C(O)— is preferably derived from lysine or arginine and corresponds to the formula:

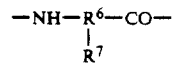

in which R$^6$ is CH and R$^7$ is —(CH$_2$)$_4$NH$_2$ or —CH$_2$)$_3$NH—C(=NH)—NH$_2$.

When the protease to be inactivated belongs to the elastase type, —AA—C(O)— is preferably derived from alanine or valine and corresponds to the formula:

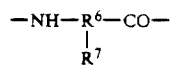

in which R$^6$ is CH and R$^7$ is —CH$_3$ or —CH(CH$_3$)$_2$.

According to the invention, the covalent chain Z is also chosen as a function of the protease to be inactivated. This chain takes account of the affinity of the fixation subsites of the natural substrates of the protease to be inactivated. Thus, the proteases have extensive active centres and it is possible to increase the effectiveness and specificity of the inhibitor by choosing a covalent chain Z fulfilling the specificity conditions of the fixation subsites.

In the case where the protease is of the trypsin, chymotrypsin or elastase type, it is possible to fulfil this specificity condition with Z complying with the formula:

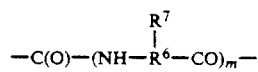

in which m=4,5 or 6 and R$^6$ and R$^7$ have the meanings given hereinbefore.

In the cyclopeptide according to the invention, the benzene nucleus forming part of the cyclopeptide can also have a substituent $R^2$, which does not modify the inactivation mechanism of the protease by the group $CH_2$. This substituent $R^2$ can be a hydrogen atom, a halogen atom or different radicals, as shown hereinbefore.

The present invention also relates to pharmaceutical compositions having the property of inhibiting a given protease, which incorporate a pharmaceutically acceptable quantity of a cyclopeptide derivative according to the invention.

The pharmaceutical compositions can be in the form of solutions, suspensions, powders or solubilizable granules, syrups or elixirs, ear, nose or eye drops, tablets, gelatin capsules, aerosols, ointments, transdermal applications or suppositories, in dosed administration forms containing non-toxic supports, adjuvants and excipients. The injections can be e.g. of the intravenous, intramuscular, subcutaneous, intradermal, intrasternal and intraarticular types, whilst infusion or instillation methods (e.g. intratracheal) can be used.

The preparations for oral use can contain one or more sweetening, flavouring or preserving agents. Tablets contain the active molecule of the cyclopeptide derivative mixed with non-toxic and pharmaceutically acceptable excipients. Among the excipients, reference can e.g. be made to inert diluents, such as calcium carbonate or sodium carbonate, calcium phosphate or sodium phosphate and lactose; agents permitting the granulation and disintegration, e.g. corn starch, fixing agents, e.g. gelatin and starch; lubricating agents, e.g. talc or magnesium stearate, etc. The tablets may or may not be coated (e.g. with the aid of glycerol distearate or monostearate) in order to delay their disintegration and absorption.

The gelatin capsules can be in the form of a hard capsule containing the active molecule mixed with an inert solid (kaolin, calcium carbonate), or a soft capsule in which the cyclopeptide derivative is mixed with water or a fatty substance (e.g. liquid paraffin).

Aqueous suspensions containing cyclopeptide derivatives and appropriate excipients, with optionally one or more preservatives (e.g. ethyl-p-hydroxybenzoate), colouring agents, sweetening agents and flavouring agents can be produced. Among the excipients, reference can be made to suspending agents (e.g. methyl cellulose and acacia gum), dispersing or wetting agents, such as e.g. natural phosphatides (example lecithin) or products for condensing ethylene oxide with various partial esters of fatty acids or aliphatic alcohols. Oily suspensions of the active molecule can be prepared by using a vegetable oil (e.g. olive oil) or a mineral oil (e.g. liquid paraffin), optionally in the presence of sweetening and flavouring agents such as those referred to hereinbefore, as well as preservatives (in particular an antioxidant).

Syrups and elixirs could contain sweetening agents (e.g. sucrose and sorbitol), one or more preservatives and flavouring agents. Granules or powders which can be suspended in water can be obtained by mixing cyclopeptide derivatives with a wetting or dispersing agent, one or more preservatives and various excipients. Emulsions of cyclopeptide derivatives in water can be produced by using a mineral or vegetable oil and various emulsifiers, such as e.g. natural gums, natural phosphatides and various esterified fatty acids.

The cyclopeptide derivatives can also be present in the form of aqueous or oily, sterile injectable suspensions using the suspending or wetting agents described hereinbefore. The solvents, diluents or excipients can e.g. be 1,3-butane diol, an isotonic sodium chloride solution, water, etc. The suppositories containing the active principle can be prepared with conventional excipients in this field such as polyethylene glycol or coco butter. For local uses, ointments, creams, gels, suspensions, solutions, etc. containing the active principle can be prepared.

Doses of 0.1 to 40 mg/kg of body weight and day can be proposed, bearing in mind that the dose for a given patient can depend on a certain number of factors, such as e.g. the efficacy of the cyclopeptide derivative in question, the age, the weight, the administration method, the diet, medicamentous interaction and the gravity of the illness.

These compositions can be used in the pathologies referred to hereinbefore. The cyclopeptide derivatives according to the invention can be prepared by conventional processes.

Thus, it is possible to prepare cyclopeptide derivatives in which $R^3$ represents NH from a derivative of formula (II):

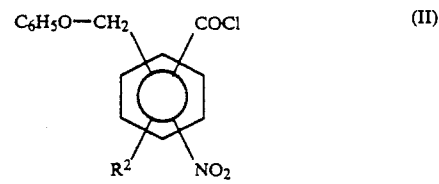

performing the following successive steps:

a) Reaction of the compound of formula (II) with $HZ^1OC_2H_5$ to obtain the compound of formula (III):

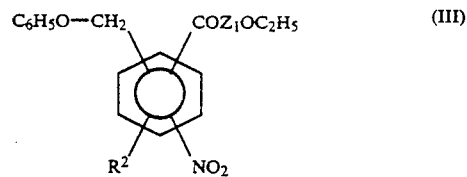

b) Reaction of the compound of formula (III) with hydrogen to obtain the compound of formula (IV):

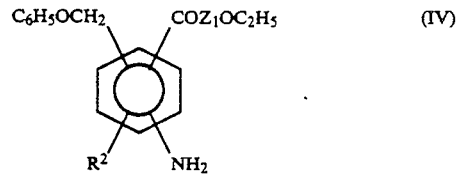

c) Reaction of the compound of formula (IV) with protected amino acid corresponding to AA—C(O), which is e.g. in accordance with the formula:

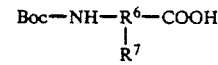

in which Boc represents the tert butyl oxycarbonyl protective group.

This reaction can be carried out using dicyclohexyl carbodiimide (DCC) and leads to the following compound of formula (V):

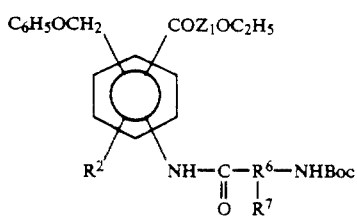

d) Reaction of the compound of formula V with hydrazine hydrate in a solvent such a methanol to obtain the compound of formula (VI):

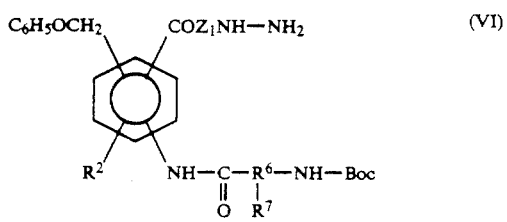

e) Reaction of the compound of formula (VI) with trifluoroacetic acid to obtain the compound of formula (VII):

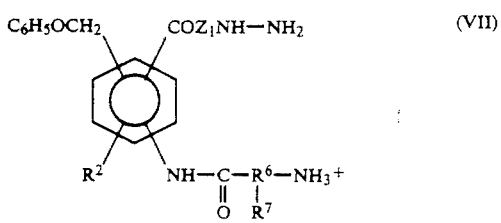

f) Reaction of the compound of formula (VII) with nitrous acid or alkyl nitrite to obtain the compound of formula (VIII):

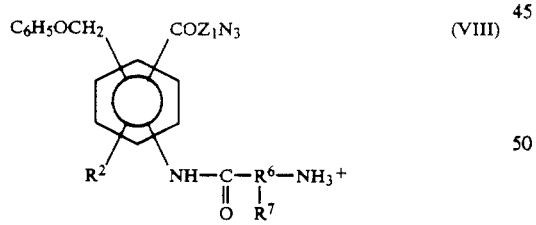

g) Reaction of the compound of formula (VIII) with a tertiary amine such as diisopropylethyl amine to obtain the cyclopeptide derivative of formula (IX):

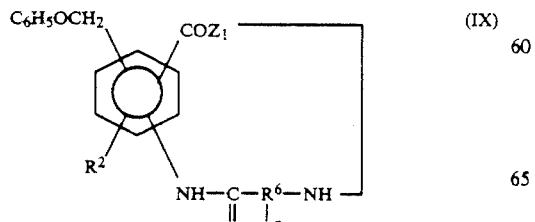

From the compound of formula (IX) it is possible to obtain the compound of formula (I) by reaction with appropriate reagents chosen as a function of the nature of the group $R^1$ used.

In the case where $R^1$ is Br, the compound of formula (IX) is reacted with hydrobromic acid and acetic acid, which makes it possible to obtain the compound of formula (X):

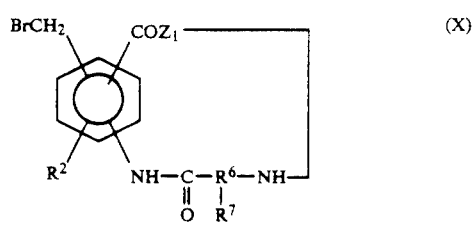

In the case where it is wished to obtain a cyclopeptide derivative of formula (I) with $R^1$ representing chlorine, the bromo derivative of formula (X) is reacted with sodium acetate in dimethyl formamide (DMF), which leads to the derivative of formula (XI):

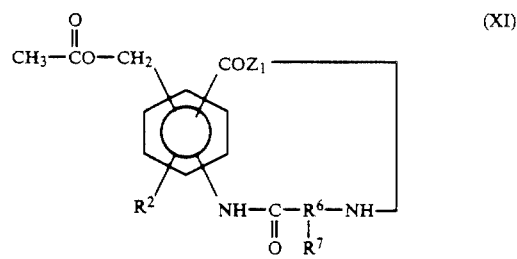

which is then transformed into a derivative of formula (XII) by reaction with methanol and triethyl amine:

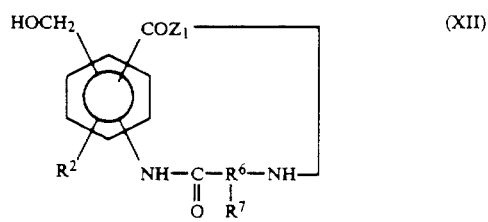

By then reacting the derivative of formula (XII) with thionyl chloride, the chloro derivative of formula (XIII) is obtained:

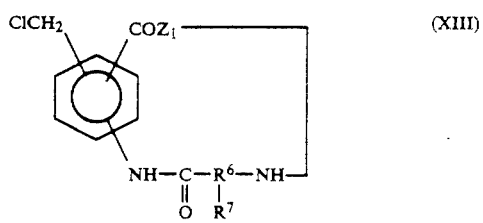

When it is wished to obtain the cyclopeptide derivative of formula (I), in which $R^1$ represents $OSO_2R^4$, the bromo derivative of formula (X) is reacted with the silver salt of sulphonic acid $R^4 SO_3H$, which makes it possible to obtain the derivative of formula (XIV):

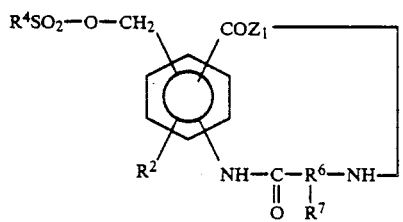

In the same way a silver salt of a phosphinic acid leads to derivatives in which $R^1=OP(O)R^4{}_2$ (formula I). The action of a dialkyl sulphide on the bromo derivative gives the corresponding sulphonium salt (I; $R^1=S^+R^4{}_2$).

However, preference is given to the preparation of cyclopeptide derivatives, in which $R^1$ represents $S^+R^4{}_2X^-1/v$ from the corresponding derivatives of formula (IX) by reacting the latter with $SR^4{}_2$ and the acid of formula $XH_v$, in accordance with the following reaction diagram:

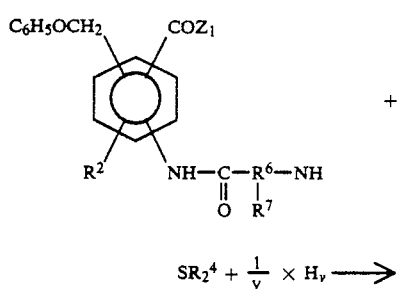

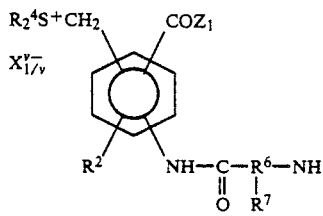

For example, $SR^4{}_2$ can represent thioanisole $CH_3SC_6H_5$ or dimethyl sulphide $CH_3SCH_3$.

The starting product of formula (II) can be obtained from the corresponding methylated nitrobenzoic acid, following the esterification of the acid function, by reacting with N-bromosuccinimide in order to form the derivative of formula (XV):

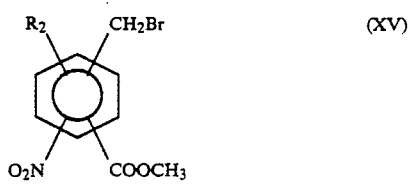

which is then reacted with a sodium phenate and then with potassium and then with $SOCl_2$ in the presence of dimethyl formamide in order to form the compound of formula (II), in accordance with the following reaction diagram:

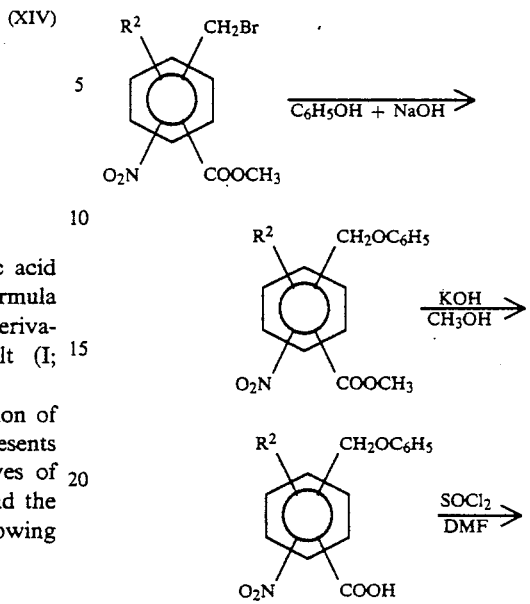

The invention will be better understood from studying the following examples which are given in an illustrative and non-limitative manner.

EXAMPLE 1

Preparation of the Cyclopeptide Derivative of Formula

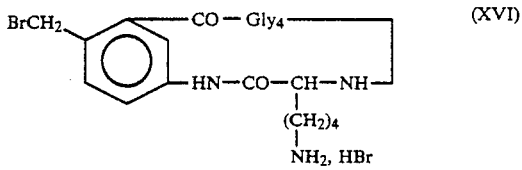

This formula corresponds to a cyclopeptide derivative of formula (I), in which $R^1$ represents bromine, $R^2$ a hydrogen atom, Z represents $CO(Gly)_4$, $R^4$ represents NH and C(O)—AA is derived from lysine.

1) Preparation of the compound of formula (II) with $R^2=H$; COCl in the meta position with respect to $NO_2$ and $C_6H_5OCH_2$ in the para position with respect to $NO_2$

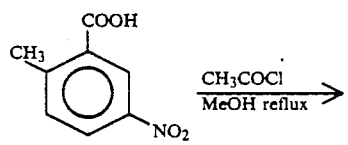

-continued

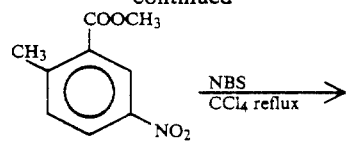

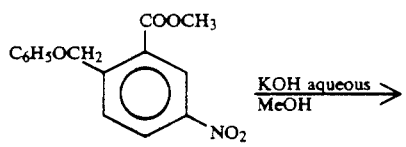

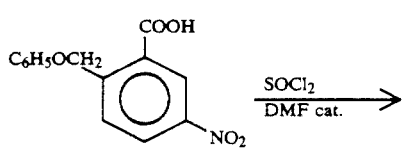

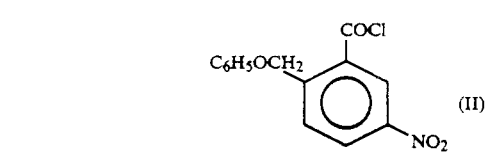

$$\underset{\underset{NO_2}{\bigodot}}{\overset{\overset{COCl}{|}}{C_6H_5OCH_2}} \quad (II)$$

11.7 g (63.6 mmoles) of 3-nitro-6-methyl benzoic acid are esterified into the corresponding methyl ester by an acetyl chloride excess in methanol under reflux. The ester obtained is dissolved in 150 ml of CCl₄ and treated with 12.5 g (70 mmoles) of N-bromosuccinimide (NBS) and 0.11 g of benzoyl peroxide under reflux for 24 hours. The reaction mixture is filtered on frit and the filtrate evaporated to dryness under reduced pressure. The crude product obtained of formula (BrCH₂) (NO₂) C₆H₃—COOCH₃ is directly treated, without prior purification, by 12 g (127 mmoles) of phenol and 2.50 g (6.2 mmoles) of aliquat (tricapryl methyl ammonium chloride) in 250 ml of CH₂Cl₂, to which are added 5.08 g (127 mmoles) of soda in pellet form dissolved in 250 ml of water. The reaction mixture is vigorously stirred at ambient temperature for 5 hours. The organic phase is then separated, washed with 400 ml of water, dried on MgSO₄, filtered, concentrated to approximately 150 ml and then undergoes chromatography on a silica column (Merck silica gel 60), whilst eluting with methylene chloride (CH₂Cl₂). A fraction of approximately 600 ml is collected, which is evaporated to dryness. The residue obtained is dissolved in 150 ml of CH₂Cl₂. There is an addition of approximately 200 ml of methanol and refluxing takes place. Crystallization is observed in the boiling solution once all the CH₂Cl₂ has evaporated. The mixture is concentrated to 150 ml and left at ambient temperature overnight. The white crystals are filtered on a Büchner filter, abundantly rinsed with methanol and dried in air. This gives 11.1 g of crystals corresponding to the derivative (C₆H₅OCH₂) (NO₂) C₆H₃—COOCH₃. The yield is 60% based on the starting acid (CH₃) (NO₂) C₆H₃—COOH. Melting point: 114° C. NMR ¹H spectrum (CDCl₃/TMS): 8.93, d (J=2 Hz), 1H (ArH₁); 8.45, dd (J=2 Hz and 8 Hz); 1H (ArH₂); 8.07, d (J=8 Hz), 1H (ArH₃); 6.8 to 7.5, m, 5H (C₆H₅O); 5.58, s, 2H (ArCH₂O); 4.00, s, 3H (COOCH₃).

| Elementary analysis | C | H | N |
|---|---|---|---|
| Calculated for C₁₅H₁₃NO₅ | 62.71 | 4.56 | 4.88 |
| Found | 62.92 | 4.31 | 4.98 |

3.59 g (12.5 mmoles) of the preceding ester are saponified by 25 ml of 4N aqueous KOH (100 mmoles) in 100 ml of methanol. The mixture is stirred at ambient temperature for 4 hours. 150 ml of water are added and the methanol is evaporated at 35° C. under reduced pressure. The aqueous solution is extracted with 100 ml of CH₂Cl₂ and then acidified by an excess of concentrated hydrochloric acid. The resulting precipitate is dissolved in 400 ml of CH₂Cl₂. The organic phase is separated, washed with 200 ml of water, dried on MgSO₄, filtered and evaporated to dryness, leading to 2.79 g of acid of formula (C₆H₅OCH₂) (NO₂) C₆H₃—COOH obtained in the form of pale yellow crystals. The yield is 82%. Melting point: 170° C. NMR ¹H spectrum (acetone d₆): 8.93, d (J=2 Hz), 1H (ArH₁); 8.55, dd (J=2 Hz and 8 Hz), 1H (ArH₂); 8.15, d (J=8 Hz), 1H (ArH₃); 6.8 to 7.7, m, 5H (C₆H₅O—); 5.71, s, 2H (ArCH₂O).

| Elementary Analysis | C | H | N |
|---|---|---|---|
| Calculated for C₁₄H₁₁NO₅ | 61.54 | 4.06 | 5.12 |
| Found | 61.98 | 3.84 | 5.12 |

2.79 g (10.2 mmoles) of the preceding acid are treated by 50 ml of SOCl₂ and 10 drops of dimethyl formamide (DMF). The clear solution obtained is stirred for 2 hours at ambient temperature and then evaporated to dryness under reduced pressure at 40° C. The residue obtained corresponds to acid chloride of formula (II): (C₆H₅OCH₂) (NO₂) C₆H₃—CO—Cl and is directly used, without purification, in the following stage (2).

2) Preparation of the compound of formula (XVII)

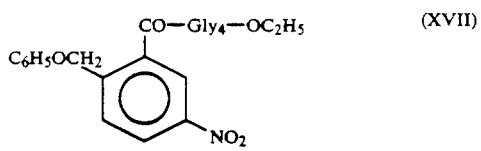

3.57 g (10 mmoles) of compound H—Gly₄—OC₂H₅ HBr and 50 ml of DMF are stirred and cooled to 0° C. 3 ml (21 mmoles) of triethyl amine are added. The mixture is stirred for 10 minutes and then a solution of 10.2 mmoles of acid chloride (II) with R²=H, COCl in the meta position with respect to NO₂ and C₆H₅O—CH₂ in the para position with respect to NO₂, obtained in (1), in 40 ml of DMF is added dropwise in approximately 30 minutes at 0° C. Following the addition, stirring is continued at ambient temperature overnight. The mixture is evaporated to dryness at 50° C. under reduced pressure. The residue obtained is triturated in 200 ml of water and the resulting precipitate filtered on the Büchner filter, washed successively with 200 ml of H₂O, 200 ml of 0.5N HCl, 100 ml of H₂O, 200 ml of 5% NaHCO₃ and 200 ml of H₂O, dried in air and then triturated in 50 ml of methanol, filtered on the Büchner filter, rinsed with methanol and then with ether, dried in air and this leads to 3.83 g (yield 72%) of compound (XVII), whose melting point is 197° to 200° C. and which is used as it is in the following stage (3). An analytical sample is prepared from 52 mg of the preceding sample, dissolved in 1 ml of DMF by crystallization following aqueous methanol addition. 34 mg of crystals are obtained having a melting point of 199° to 203° C. Analysis by NMR $^1$H gives the following results: (DMSO-d$_6$): 9.09, t (J=5.6 Hz), 1H (NH Gly); 8.42, d (J=2 Hz), 1H (ArH); 8.36, dd (J=2 Hz and 8.6 Hz), 1H (Ar Hz); 8.34, t (masked), 1H (NH Gly); 8.28, t (J 5.8 Hz), 1H (NH Gly); 8.23, t (J=5.8 Hz), 1H (NH Gly); 7.88, d (J=8.6 Hz), 1H (ArH$_3$); 7.3, m, 2H (C$_6$H$_5$O—); 7.0, m, 3H (C$_6$H$_5$—O—); 5.39, s, 2H (C$_6$H$_5$O—CH$_2$Ar); 4.06, q (J=7.1 Hz), 2H (O—CH$_2$CH$_3$); 3.96, d (J=5.5 Hz), 2H (CH$_2$Gly); 3.81, d (J=5.5 Hz), 4H (2CH$_2$Gly); 3.75, d (J=5.6 Hz), 2H (CH$_2$Gly); 1.17, t (J=7.1 Hz), 3H (OCH$_2$CH$_3$).

| Elementary Analysis | C | H | N |
|---|---|---|---|
| Calculated for C$_{24}$H$_{27}$N$_5$O$_9$ 0.5 H$_2$O | 53.52 | 5.24 | 13.00 |
| Found | 53.48 | 5.09 | 12.50 |

3) Preparation of the compound of formula (XIX) with lysine, whose αNH$_2$ group is protected by a tert butyloxy carbonyl group Boc and whose εNH$_2$ group is protected by a benzyloxy carbonyl group CBZ

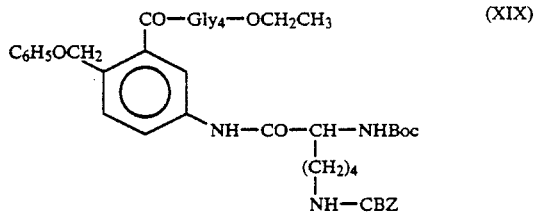

(Boc = (CH$_3$)$_3$C—O—CO—),
(CBZ = C$_6$H$_5$—CH$_2$—O—CO—).

Firstly, 1.06 g (2 mmoles) of the peptide of formula (XVII) are dissolved in 25 ml of DMF hot. This is followed by the addition of 75 ml of methanol and 150 mg (0.7 mmole) of PtO$_2$. The mixture is hydrogenated for 2 hours at ambient temperature, under 3 atmospheres using a Parr apparatus. The catalyst is filtered and the solvents evaporated under reduced pressure giving the compound of formula (XVIII):

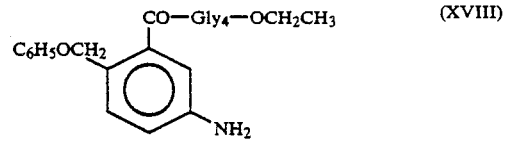

whose chromatographic analysis gives a R$_F$ of 0.46 (support: silica, eluent CH$_2$Cl$_2$ 85%—MeOH 15%). The presence of an aromatic amine function leads to a fluorescent ultraviolet absorption at 366 nm of the chromatographic spot. This compound is not very stable in solution and is therefore used immediately after preparation, without further purification, for the synthesis of compound (XIX).

Thus, the aromatic amine of formula (XVIII) previously obtained is dissolved in 1 ml of DMF, 25 ml of CH$_2$Cl$_2$ are added and the solution cooled to −5° C. This is followed by the addition of 0.912 g (2.4 mmoles) of Nα-Boc-Nε-CBZ-L-lysine, then 0.495 g (2.4 mmoles) of dicyclohexyl carbodiimide (DCC) in 25 ml of CH$_2$Cl$_2$. The mixture is stirred at −5° C. for 2 hours and then at ambient temperature overnight. The dicyclohexyl urea precipitate formed is then filtered and the solvents evaporated. The residue is dissolved in 400 ml of ethyl acetate and the organic phase is successively extracted with 200 ml of 5% NaHCO$_3$, 200 ml of H$_2$O, 200 ml of 0.5N HCl, 200 ml of H$_2$O, dried on MgSO$_4$, filtered and evaporated to dryness. The peptide obtained is purified on a silica column (silica gel 60) using as the eluent a mixture of methanol and CH$_2$Cl$_2$ in proportions 10%:90%.

This gives the derivative of formula (XIX) with a 71% yield. The chromatographic analysis on silica gives an R$_F$ of 0.70 (eluent: methanol 15%—CH$_2$Cl$_2$ 85%) or 0.29 (eluent: methanol 10%—CH$_2$Cl$_2$ 90%). The melting point is 72° to 76° C. The rotary power is $[\alpha]_{546\ nm}^{25°\ C.}=-9.1°$ (c 0.5; MeOH).

Analysis by NMR $^1$H gives the following results: (CD$_3$OD): 8.07, s, 1H (ArH$_1$); 7.81, d (J=8.3 Hz), 1H (ArH$_2$); 7.71, d (J=8.3 Hz), 1H (ArH$_3$); 7.51, m, 5H (ArH of CBZ); 7.44, m, 2H (C$_6$H$_5$O—); 7.13, m, 3H (C$_6$H$_5$O—); 5.42, s, 2H (C$_6$H$_5$O—CH$_2$—Ar); 5.23, s, 2H (CH$_2$ of CBZ); 4.35, m, 1H (CHαLys); 4.29, q (J=7.1 Hz), 2H (CH$_2$ of OEt); 4.24, s, 2H (CH$_2$Gly); 4.09, s, 2H (CH$_2$Gly); 4.08, s, 2H (CH$_2$Gly); 4.07, s, 2H (CH$_2$Gly); 3.31, m, 2H (CH$_2$εLys); 1.91, m, 2H (CH$_2$βLys); 1.70, m, 4H (CH$_2$j and CH$_2$δ of Lys); 1.63, s, 9H (3CH$_3$ of Boc); 1.40, t (J=7.1 Hz), 3H (CH$_3$ of OEt).

| Elementary Analysis | C | H | N |
|---|---|---|---|
| Calculated for C$_{43}$H$_{55}$N$_7$O$_{12}$ | 59.92 | 6.43 | 11.38 |
| Found | 59.77 | 6.55 | 11.21 |

4) Preparation of the Derivative of Formula (XX)

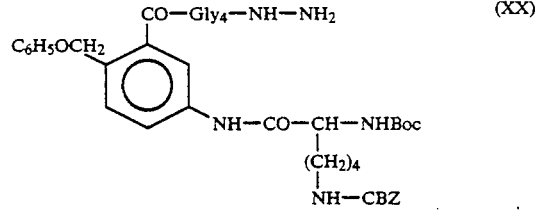

3.2 g (3.7 mmoles) of ester of formula (XIX) in solution in 150 ml of methanol are stirred in the presence of 5.25 ml (108 mmoles) of hydrazine hydrate H$_2$NNH$_2$, H$_2$O at ambient temperature for 12 hours. The solution is evaporated under reduced pressure at 40° C. The residue is taken up several times with methanol and evaporation to dryness takes place until the hydrazine has been completely entrained. The solid residue is triturated in ether and the supernatant removed. After drying, 3.109 g of derivative (XX) is obtained in the form of a white powder. The yield is 98%. The melting point is 100° to 110° C.

Chromatographic analysis on a silica support gives a R$_F$ of 0.46 (eluent: methanol 20%—CH$_2$Cl$_2$ 80%). The rotary power is $[\alpha]_{546}^{25°\ C.}=-8.4°$ (c 0.6; MeOH).

Analysis by NMR $^1$H gives the following results: (CD$_3$OD/TMS): 7.88, d (J=1.8 Hz), 1H (ArH$_1$); 7.62, dd (J=1.8 Hz and 8.4 Hz), 1H (ArH$_2$); 7.53, d (J=8.4 Hz), 1H (ArH$_3$); 7.30, m, 5H (ArH of CBZ); 7.24, m 2H ($C_6H_5O$—); 6.94, m, 3H ($C_6H_5O$—)); 5.22, s, 2H ($C_6H_5OCH_2Ar$); 5.04, s, 2H ($CH_2$ of CBZ); 4.15, m, 1H (CHα of Lys); 4.06, s, 2H ($CH_2$ of Gly); 3.88, s, 2H ($CH_2$ of Gly); 3.87, s, 2H ($CH_2$ of Gly); 3.84, s, 2H ($CH_2$ of Gly); 3.12, m, 2H ($CH_2\epsilon$ of Lys); 1.75, m, 2H ($CH_2\beta$ of Lys); 1.51, m, 4H ($CH_2\gamma$ and $CH_2\delta$ of Lys); 1.43, s, 9H (3$CH_3$ of Boc).

| Elementary Analysis | C | H | N |
|---|---|---|---|
| Calculated for $C_{41}H_{53}N_9O_{11}$, 0.5 $H_2O$ | 57.46 | 6.35 | 14.71 |
| Found | 57.36 | 6.37 | 14.46 |

5) Preparation of the derivative of formula (XXI)

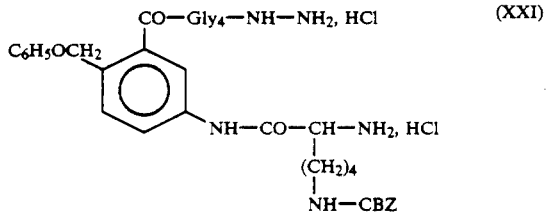

3.109 g (3.7 mmoles) of the compound of formula (XX) are dissolved in 80 ml of glacial acetic acid and addition takes place of 20 ml of a 2M hydrochloric acid solution in acetic acid. After stirring for 30 minutes, 150 ml of ethyl ether are added. The precipitate is allowed to settle and the supernatant removed. The residue is rinsed three times with ethyl ether, the supernatant being removed on each occasion after settling. The residual precipitate is dissolved in 100 ml of methanol and the solution is evaporated to dryness under reduced pressure at 40° C. This operation is repeated a second time. The residue is triturated in ethyl ether until a homogeneous white powder is obtained. The supernatant ether is eliminated and the residual solid dried in vacuo. This gives 2.947 g of derivative of formula (XXI) in the form of white powder.

The yield is 98% and the melting point 84° to 88° C. (decomposition). Chromatographic analysis on a silica support gives an $R_F$ of 0.07 (eluent: MeOH 20%—$CH_2Cl_2$ 80%) or 0.62 (eluent: ethyl acetate/n-butanol/acetic acid/water in proportion 1:1:1:1).

The rotary power is $[\alpha]_{546}^{25°}$ $C.=+23.0°$ (c 0.5; MeOH).

Analysis by NMR $^1H$ gives the following results: ($CD_3OD$/TMS): 7.93, d (J=2.1 Hz), 1H ($ArH_1$); 7.71, dd (J=2.1 Hz and 8.4 Hz) 1H ($ArH_2$); 7.56, d (J=8.4 Hz), 1H ($ArH_3$); 7.31, m, 5H (ArH of CBZ); 7.25, m, 2H ($C_6H_5O$—); 6.94, m, 3H ($C_6H_5O$—); 5.24, s, 2H ($C_6H_5O$—$CH_2$—Ar); 5.01, s, 2H ($CH_2$ of CBZ); 4.07, s, 2H ($CH_2$ of Gly); 4.03, m, 1H (CHα of Lys); 3.95, s, 2H ($CH_2$ of Gly); 3.91, s, 2H ($CH_2$ of Gly); 3.89, s, 2H ($CH_2$ of Gly); 3.14, m, 2H ($CH_2\epsilon$ of Lys); 1.97, m, 2H ($CH_2\beta$ of Lys); 1.53, m, 4H ($CH_2\gamma$ and $CH_2\delta$ of Lys).

6) Preparation of the Cyclopeptide of Formula (XXII)

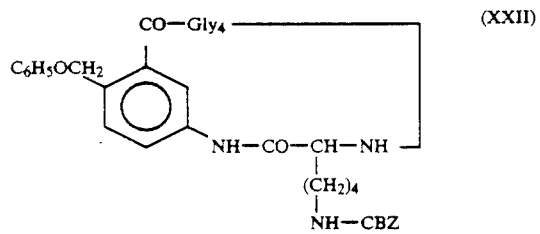

A solution of 0.820 g (1 mmole) of the compound of formula (XXI) is brought into 20 ml of DMF at approximately −30° to −40° C. Acidification then takes place by the addition of 1.45 ml (8 mmoles) of a 5.5M hydrochloric acid solution in THF, followed by the addition of 0.200 ml (1.5 mmole) of isoamyl nitrate. The solution is stirred at approximately −35° C. for 30 minutes and then diluted by adding 200 ml of cold DMF. The solution is alkalized to a pH of 8 to 9 by adding 2.1 cm³ (12 mmoles) of diisopropyl ethyl amine, stirred at −35° C. for 10 minutes and then left to stand in a refrigerator (+4° C.) for 24 hours. These operations are repeated several times in order to treat in all 3.13 g (3.82 mmoles) of the compound of formula (XXI).

The reaction mixtures are then combined and 200 ml of a 5% aqueous $K_2CO_3$ solution are added. Concentration takes place to approximately 150 ml under a reduced pressure and at 40° C., in order to eliminate the diisopropyl ethyl amine, the water and part of the DMF. The mixture is then filtered on frit to eliminate the insoluble mineral salts and the filtrate is evaporated to dryness under reduced pressure at 40° C. The residue is an oil which crystallizes. By adding 50 ml of methanol, white crystals are obtained, which are filtered on a Büchner filter, rinsed with methanol and dried (weight obtained 1.798 g). The filtrate is evaporated to dryness and the residue undergoes chromatography on a silica column (silica gel 60) using as the eluent a solution of methanol/$CH_2Cl_2$ in a proportion of 15%:85%. The fractions containing the product are combined and the solvents evaporated. The residue is crystallized in methanol as previously. Thus, 0.076 g of crystals are obtained, i.e. in all 1.874 g of cyclopeptide of formula (XXII).

The yield is 68% and the melting point 270° to 280° C. (decomposition). Chromatographic analysis on a silica support gives an $R_F$ of 0.55 (eluent: MeOH 20%—$CH_2Cl_2$ 80%) or 0.78 (eluent: EtOAc:1/n-BuOH:1/AcOH:1/$H_2O$:1). The corresponding spot is negative to ninhydrin. The rotary power is $[\alpha]_{546}^{25°}$ $C.=-40.6°$ (c 0.5; DMF).

Analysis by NMR $^1H$ gives the following results: (DMSO d6): 9.03, s, 1H (ArNHCO); 8.89, t (J=5.7 Hz), 1H (NH Gly); 8.75, t, (J=4.7 Hz), 1H (NH Gly); 8.58, d (J=7.4 Hz), 1H (NH Lys); 8.20, dd (J=1.6 Hz and 8.4 Hz), 1H ($ArH_2$); 8.16, t (J=6.0 Hz), 1H (NH Gly); 7.75, t (J=5.6 Hz), 1H (NH Gly); 7.71, D (J=2.0 Hz), 1H ($ArH_1$); 7.50, d (J=8.5 Hz), 1H ($ArH_3$); 7.34, m, 5H (ArH of CBZ); 7.29, m, 2H ($C_6H_5O$—); 6.94, m, 3H ($C_6H_5O$); 5.21, s, 2H ($C_6H_5OCH_2$—Ar); 5.00, s, 2H ($CH_2$ of CBZ); 4.20, m, 1H (CH α of Lys); 4.10 to 3.60, m, 8H (4$CH_2$ of Gly); 3.00, m, 2H ($CH_2$ ε of Lys); 1.93, m, 1H and 1.67, m, 1H ($CH_2$ β of Lys); 1.41, m, 4H ($CH_2$ γ and $CH_2$ δ of Lys).

| Elementary Analysis | C | H | N |
| --- | --- | --- | --- |
| Calculated for $C_{36}H_{41}N_7O_9$ | 60.41 | 5.77 | 13.70 |
| Found | 60.40 | 5.70 | 13.43 |

7) Preparation of Cyclopeptide of Formula (XVI)

A mixture of 0.145 g (0.2 mmole) of cyclopeptide of formula (XXII) and 20.4 ml of acetic acid is heated until a clear solution is obtained and is then cooled to ambient temperature. This is followed by the addition of 3.6 cm³ of a 33% HBr solution in acetic acid. The mixture is stirred at ambient temperature for 1 hour. 25 cm³ of ethyl ether are then added, which leads to the precipitation of the brominated cyclopeptide. After settling the supernatant is removed. The precipitate is then stirred in ether and then centrifuged, the supernatant then being removed. This operation is repeated several times in order to eliminate all the acids from the medium. The precipitate is then dried in vacuo. This gives 0.131 g of cyclopeptide of formula (XVI) in the form of a white powder. The yield is 99% and the melting point 190° to 200° C. (decomposition).

Chromatographic analysis on a silica support gives a $R_F$ of 0.43 (eluent: EtOAc:1/nBuOH:1/AcOH:1/H$_2$O:1). The spot is negative to ninhydrin. The rotary power is $[\alpha]_{546}^{25°\ C.} = 35.5°$ (c 0.2; MeOH).

Analysis by NMR $^1$H gives the following results: (CD$_3$OD): 8.27, dd (J=2.2 Hz and 8.4 Hz), 1H (ArH$_2$); 7.93, d (J=2.2 Hz), 1H (ArH$_1$); 7.66, d (J=8.4 Hz), 1H (ArH$_3$); 5.03, d (J=10.1 Hz) and 4.98, d (J=8.1 Hz), 2H (BrCH$_2$Ar); 4.59, dd (J=4.4 Hz and 9.7 Hz), 1H (CH α of Lys); 4.38, d (J=16.9 Hz) and 4.13, d (J=16.9 Hz), 2H (CH$_2$ of Gly); 4.30, s, 2H (CH$_2$ of Gly); 4.24, d (J=16.9 Hz) and 4.13, d (J=16.9 Hz), 2H (CH$_2$ of Gly); 4.15, d (J=15.8 Hz) and 4.01, d (J=15.8 Hz), 2H (CH$_2$ of Gly); 3.15, t (J=7.5 Hz), 2H (CH$_2$ ε of Lys); 2.25, m, 1H and 2.03, m, 1H (CH$_2$ β of Lys); 1.89, m, 2H (CH$_2$ δ of Lys); 1.74, m, 2H (CH$_2$ γ of Lys).

| Elementary Analysis | C | H | N |
| --- | --- | --- | --- |
| Calculated for $C_{22}H_{31}N_7O_6Br_2$ | 40.69 | 4.81 | 15.10 |
| Found | 40.88 | 5.01 | 13.64 |

Mass spectrum (FAB>0): 568 (MH+ for $^{79}$Br); 570 (MH+ for $^{81}$Br).

EXAMPLE 2

The properties of the cyclopeptide derivative of formula (XVI) are checked and in particular its capacity to inactivate bovine trypsin or human urokinase using the methods of Kitz and Wilson (for trypsin and urokinase) and the method of Hart and O'Brien (for trypsin), 1973, published in Biochemistry, 12, pp. 2940–2945.

The apparent inactivation constant $k_i/K_i$ is in this case:
- 53 M$^{-1}$s$^{-1}$ for bovine trypsin and
- 4.2 M$^{-1}$s$^{-1}$ for human urokinase.

However, this cyclopeptide derivative has no action on elastase.

EXAMPLE 3

Preparation of the cyclopeptide derivative of formula (XXIII):

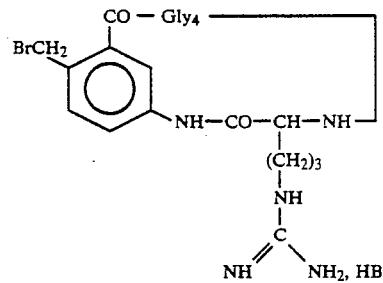

This formula corresponds to a cyclopeptide derivative of formula (I) in which R$^1$ represents bromine, R$^2$ a hydrogen atom, Z represents CO(Gly)$_4$, R$^3$ representing NH and CO —AA being derived from arginine.

An operating procedure similar to that of Example 1 is followed for preparing this cyclopeptide derivative, except that in the third stage the compound of formula (XVIII) is reacted with arginine, whose α NH$_2$ group is protected by a butyloxycarbonyl group Boc. This gives the cyclopeptide of formula (XXIII), which has the following characteristics:

$R_F$=0.52 (support: silica, eluent: EtOAc:1/nBuOH:1/AcOH:1/H$_2$O:1).

Melting point: 205° to 215° C. (decomposition).

Rotary power: $[\alpha]_{546}^{25°\ C.} = -210°$ (c 0.2; MeOH).

Analysis by nuclear magnetic resonance: (CD$_3$OD): 8.25, dd (J=2.0 Hz and 8.4 Hz), 1H (ArH$_2$); 7.96, d (J=2.0 Hz), 1H (ArH$_1$); 7.66, d (J=8.4 Hz), 1H (ArH$_3$); 5.01, s, 2H (BrCH$_2$Ar); 4.61, dd (J=4.7 Hz and 9.2 Hz), 1H (CH α of Arg); 3.9 to 4.5, m, 8H (4CH$_2$ of Gly); 3.45, m, 2H (CH$_2$ δ of Arg); 2.28, m, 1H and 2.06, m, 1H (CH$_2$ β of Arg); 1.93, m, 2H (CH$_2$ γ of Arg).

Mass spectrum (FAB>0): 596 (MH+ for $^{79}$Br) and 598 (MH+ for $^{81}$Br).

EXAMPLE 4

The properties of the cyclopeptide derivative of formula (XXIII) are checked and in particular its capacity to inactivate bovine trypsin or human urokinase using the same methods as in Example 2 and working at 25° C. with the 0.025M sodium phosphate buffer, 0.1M NaCl, 0.05% (v/v) Tween 80 and at pH 7.5 for human urokinase. The apparent inactivation constant ki/Ki is 150 M$^{-1}$s$^{-1}$ for bovine trypsin.

The apparent inactivation constant ki/Ki is 165 M$^{-1}$s$^{-1}$ for human urokinase. The inactivating or inhibiting properties of this derivative with respect to human t-PA are checked at 25° C. in a 0.05M Tris buffer, 0.038M NaCl, 0.01% (v/v) Tween 80 and pH 8.3. In this case ki/Ki is 0.3 M$^{-1}$s$^{-1}$.

However, this cyclopeptide derivative has no action on elastase.

EXAMPLE 5

Preparation of the Cyclopeptide Derivative of Formula (XXIV)

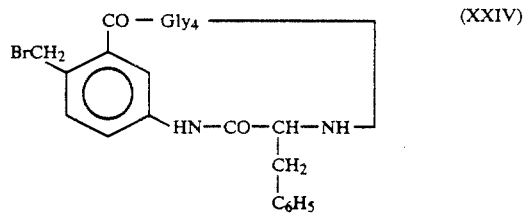

(XXIV)

This cyclopeptide derivative corresponds to a derivative of formula (I), in which $R^1$ represents bromine, $R^2$ a hydrogen atom, Z represents $CO(Gly)_4$, $R^3$ represents NH and CO —AA is derived from phenyl alanine.

In order to prepare this cyclopeptide derivative, an operating procedure similar to that of Example 1 is followed, except that in the third stage use is made of phenyl alanine, whose $NH_2$ group is protected by a butyloxycarbonyl group Boc. This gives the cyclopeptide derivative of formula (XXIV).

Its characteristics are as follows: $R_F$—0.50 (eluent: MeOH 20%—$CH_2Cl_2$ 80%); 0.69 (eluent: EtOAc:1/nBuOH:1/AcOH: 1/$H_2O$:1).

Analysis by nuclear magnetic resonance: ($CD_3OD$): 8.15, dd (J =2.1 Hz and 8.5 Hz), 1H ($ArH_2$); 7.92, d (J=2.2 H), 1H ($ArH_1$); 7.66, d (J=8.5 Hz), 1H ($ArH_3$); 7.47, m, 5H (ArH of Phe); 5.00, s, 2H ($BrCH_2Ar$); 4.86, m, 1H (CH α Phe); 3.7 to 42, m, 8H ($4CH_2$ Gly); 3.59, m, 1H and 3.20, m, 1H ($CH_2$ of Phe); ($CD_3COOD$): 8.03, d (J=8.3 Hz), 1H ($ArH_2$); 7.79, s, 1H ($ArH_1$); 7.56, d (J=8.5 Hz), 1H ($ArH_3$); 7.36, m, 5H (ArH of Phe); 4.93, dd (J=5 Hz and 10 Hz), 1H (CH α of Phe), 4.86, s, 2H ($BrCH_2Ar$); 4.43, d (J=16.4 Hz), 1H and 4.35, d (J=16.4 Hz), 1H ($CH_2$ of Gly); 4.34, d (J=16.5 Hz), 1H and 4.17, d (J=16.4 Hz), 1H ($CH_2$ of Gly); 4.27, d (J=16.6 Hz), 1H and 4.10, d (J=16.5 Hz), 1H ($CH_2$ of Gly); 4.09, d (J=16.0 Hz), 1H and 3.92, d (J=16.1 Hz), 1H ($CH_2$ of Gly); 3.47, dd (J=5 Hz and 15 Hz), 1H and 3.17, dd (J=10 Hz and 15 Hz), 1H ($CH_2$ of Phe).

Melting point: 180° to 200° C. (decomposition)

Rotary power: $[\alpha]_{546}^{25°C.} = -46.7°$ (c 0.12; DMF).

| Elementary Analysis | C | H | N |
|---|---|---|---|
| Calculated for $C_{25}H_{27}N_6O_6Br$ 3.5 $H_2O$ | 46.16 | 5.26 | 12.92 |
| Found | 46.23 | 4.71 | 11.78 |

Mass spectrum (FAB>0): 586 M* for $^{79}Br$ and 588 (M* for $^{81}Br$).

EXAMPLE 6

The properties of the cyclopeptide derivative of formula (XXIV) are checked and in particular its capacity to inactivate bovine chymotripysin using the same methods as in Example 2. The apparent inactivation constant ki/Ki is in this case 7 $M^{-1}s^{-1}$.

EXAMPLE 7

Preparation of the Cyclopeptide Derivative of Formula (XXV)

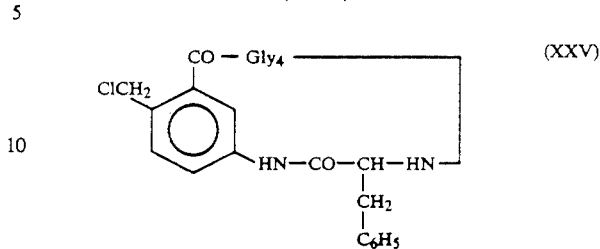

(XXV)

This derivative corresponds to a cyclopeptide derivative of formula (I), in which $R^1$ represents Cl, $R^2$ a hydrogen atom, Z represents $CO—Gly_4$, $R^3$ represents NH and CO—AA is derived from phenyl alanine.

The starting product is the cyclopeptide derivative of formula (XXIV) and it is successively treated by sodium acetate in dimethyl formamide (DMF) and then by triethyl amine in methanol and finally by thionyl chloride.

To this end, 0.025 g (0.04 mmole) of cyclopeptide of formula (XXIV) are vigorously stirred at ambient temperature in the presence of 0.300 g (3 mmoles) of potassium acetate and 3 ml of DMF. The mixture is then evaporated to dryness under reduced pressure. This is followed by the addition of 25 ml of a 20:80 methanol/methylene chloride mixture, followed by stirring for a few minutes, filtration and evaporation of the solvents. The residue undergoes chromatography on a silica column (silica gel 60), eluting with a mixture of methanol (20%) and $CH_2Cl_2$ (80%). The fractions are combined and the solvents evaporated. The residue is dissolved in 2 ml of methanol. Ether addition leads to precipitation. The precipitate is centrifuged, rinsed with ether, centrifuged again and dried. This gives 0.018 g of acetate corresponding to formula (XXVI):

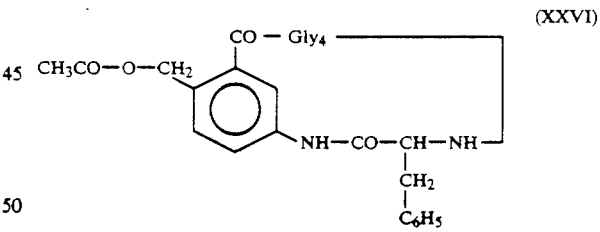

(XXVI)

The compound of formula (XXVI) obtained in this way with a yield of 75% has the following characteristics: melting point 190° to 210° C. (decomposition); $R_F$ (silica)=0.5 (eluent: MeOH 20%—$CH_2Cl_2$ 80%); 0.55 (eluent: EtOAc:1/nBuOH:1/AcOH:1/$H_2O$:1).

Analysis by nuclear magnetic resonance: ($CD_3OD$): 8.20, dd (J=2.1 Hz and 8.4 Hz), 1H ($ArH_2$); 7.93, d (J=2.2 Hz), 1H ($ArH_1$); 7.64, d (J=8.4 Hz), 1H ($ArH_3$); 7.47, m, 5H (ArH of Phe); 5.49, d (J=12.9 Hz) and 5.43, d (J=12.9 Hz), 2H ($AcOCH_2Ar$); 4.85, dd (J=4.6 Hz and 10.1 Hz), 1H (CH α of Phe); 4.32, d (J=16.7 Hz), 1H and 4.09, d (J=16.9 Hz), 1H ($CH_2$ of Gly); 4.25, s, 2H ($CH_2$ of Gly); 4.24, d (J=17.1 Hz), 1H and 4.09, d (J=16.9 Hz) 1H ($CH_2$ of Gly); 4.01, d (J=15.6 Hz), 1H and 3.82, d (J=15.7 Hz), 1H ($CH_2$ of Gly); 3.60, dd (J=4.5 Hz) and 14.0 Hz), 1H and 3.18, dd (J=10.3 Hz and 14.0 Hz), 1H (CH$_2$ of Phe); 2.25, s, 3H (CH$_3$COO—).

Rotary power: $[\alpha]_{546}^{25°}$ $^{C.}$ = $-36.9°$ (c 0.13; DMF).

Mass spectrum (FAB<0): 566 (M$^\ominus$); 600 (M—H—CH$_3$COOH)$^-$.

0.066 g (0.12 mmoles) of derivative of formula (XXVI) is dissolved in 18 ml of methanol, followed by the addition of 2 ml of triethyl amine and stirring the solution at ambient temperature for 48 hours. The mixture is then evaporated to dryness at 40° C. under reduced pressure and the residue undergoes chromatography on a silica column (silica gel 60), whilst eluting with a mixture of MeOH: 20%/CH$_2$Cl$_2$: 80%. The adequate fractions are combined and the solution concentrated to approximately 2 ml. The addition of 15 ml of ethyl ether causes a precipitation. The precipitate is centrifuged, triturated in ether and centrifuged again, followed by drying in vacuo. This gives 0.043 g of derivative of formula (XXVII) with a yield of 70%:

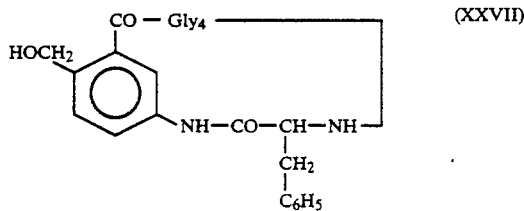

(XXVII)

The derivative of formula (XXVII) has the following characteristics:

Melting point: 200° to 220° C. (decomposition); R$_F$ (silica): 0.50 (eluent: MeOH 20%—CH$_2$Cl$_2$ 80%);

rotary power: $[\alpha]_{546}^{25°}$ $^{C.}$ = $-80.0°$ (c 0.2; DMF).

Analysis by nuclear magnetic resonance: (CD$_3$OD): 8.23, dd (J=2.2 Hz and 8.3 Hz), 1H (ArH$_2$); 8.00, d (J=2.2 Hz), 1H (ArH$_1$) 7.63, d (J=8.3 H$_X$), 1H (ArH$_3$); 7.49, m, 5H (ArH of Phe); 4.87, s, 2H (OCH$_2$Ar); 4.85, dd partly masked (J=4.4 Hz and estimated 10.6 Hz), 1H (CH $\alpha$ of Phe); 4.38, d (J=16.8 Hz), 1H and 4.11, d (J=16.8 Hz), 1H (CH$_2$ of Gly); 4.30, d (J=16.3 Hz), 1H and 4.23, d (J=16,3 Hz), 1H (CH$_2$ of Gly); 4.28, d (J=17.1 Hz), 1H and 4.00, d (J=17.1 Hz), 1H (CH$_2$ of Gly); 4.03, d (J=15.4 Hz), 1H and 3.78, d (J=15.4 Hz), 1H (CH$_2$Gly); 3.65, dd (J=4.3 Hz and 14.2 Hz), 1H and 3.17, dd (J=10.6 Hz and 14.2 Hz), 1H (CH$_2$ of Phe).

Finally, 0.0157 g (0.03 mmole) of the derivative of formula (XXVII) is dissolved in 0.5 ml of DMF. The solution is stirred at 0° C. and to it is added 0.25 ml of a freshly prepared solution maintained at 0° C. of 0.17 ml of SOCl$_2$ in 5 ml of DMF. The mixture is stirred for 1 minute at 0° C. and then 3 minutes at ambient temperature and is then immediately evaporated to dryness under reduced pressure. These operations are repeated several times to treat in all 0.0443 g (0.08 mmole) of the derivative of formula (XXVII). The residues obtained after evaporation of the solvents are combined.

Purification takes place by silica column chromatography, whilst eluting with a mixture of MeOH 15%—CH$_2$Cl$_2$ 85%. The adequate fractions are combined and the solution evaporated to dryness. The residue is dissolved in 2 ml of methanol and precipitated by ethyl ether addition. The precipitate is centifuged, triturated in ether, centrifuged again and dried in vacuo. This gives 0.0268 g of chloride of formula (XXV) with a yield of 58%. The derivative of formula (XXV) has the following characteristics: melting point: 170° to 230° C. (decomposition in the solid state);

R$_F$(silica): 0.67 (eluent: MeOH 20%—CH$_2$Cl$_2$ 80%); 0.74 (eluent: EtOAc:1/nBuOH:1/AcOH:1/H$_2$O:1).

Rotary power: $[\alpha]_{546}^{25°}$ $^{C.}$ = $-31.8°$ (c 0.8; MeOH).

Analysis by nuclear magnetic resonance: (CD$_3$OD): 8.17, dd (J=2.1 Hz and 8.4 Hz), 1H (ArH$_2$); 7.94, d (J=2.1 Hz), 1H (ArH$_1$); 7.68, d (J=8.4 Hz), 1H (ArH$_3$); 7.48, m, 5H (ArH of Phe); 4.86 dd (J=4.7N$_Z$ and 10.0 Hz), 1H (CH $\alpha$ of Phe); 4.83, s, 2H (ClCH$_2$Ar); 4.32, d (J=17.0 Hz), 1H and 4.12, d (J=17.0 Hz), 1H (CH$_2$ of Gly); 4.29, s, 2H (CH$_2$ of Gly); 4.23, d (J=16.9 Hz), 1H and 4.09, d (J=16.8 Hz), 1H (CH$_2$ of Gly); 4.01, d (J=15.8 Hz), 1H and 3.85, d (J=15.8 Hz), 1H (CH$_2$ of Gly); 3.59, dd (J=4.7 Hz and 14.0 Hz), 1H and 3.19, dd (J=10.1 Hz and 14.0 Hz), 1H (CH$_2$ of Phe).

| Elementary Analysis | C | H |
|---|---|---|
| Calculated for C$_{25}$H$_{27}$N$_6$O$_6$Cl, 1.5 H$_2$O | 52.68 | 5.31 |
| Found | 52.43 | 4.69 |

Mass spectrum (DCI): 542 (M° for $^{35}$Cl); 544 (M° for $^{37}$Cl).

EXAMPLE 8

The properties of the cyclopeptide derivative of formula (XXV) are checked and in particular its capacity to inactivate bovine chymotrypsin by using the same methods as in Example 2. The apparent inactivation constant k$_i$/K$_i$ is in this case 2.8M$^{-1}$s$^{-1}$.

The results of Examples 2,4,6 and 8 are summarized in the attached Table 1.

EXAMPLE 9

Preparation of the Cyclopeptide of Formula (XXVIII)

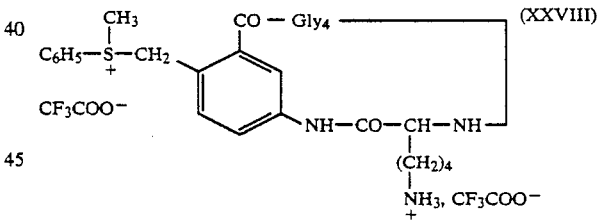

(XXVIII)

A solution of 0.100 g (0.14 mmole) of cyclopeptide of formula (XXII) and 1.412 cm$^3$ (14 mmoles) of thioanisole in 5.6 cm$^3$ of trifluoroacetic acid (TFA) is stirred at ambient temperature for 24 h. This is followed by the addition of 50 cm$^3$ of ethyl ether, which leads to the formation of a white precipitate. The precipitate is decanted and the supernatant removed. The precipitate is rinsed several times with ether, collected by centrifuging, dried in vacuo and purified by silica column chromatography (silica gel 60), whilst eluting with a solution EtOAc/nBuOH/AcOH/H$_2$O 1:1:1:1. The adequate fractions are combined and the solution evaporated to dryness under reduced pressure. The residue obtained is dissolved in 2 cm$^3$ of trifluoroacetic acid and then precipitated with ether. The precipitate is rinsed several times with ether, collected by centrifuging and dried. It is dissolved in 2 cm$^3$ of methanol, reprecipitated with ether, rinsed several times with ether, collected by centrifuging and dried. It is then dissolved in 10 cm$^3$ of water. The solution is filtered and then lyophilized. This gives 0.056 g of cyclopeptide of formula (XXVIII) in the form of a white powder. The yield is 48% and the melting point 135° C. (with decomposition). Chromatographic analysis on a silica support gives a Rf of 0.12 (eluent EtOAc/nBuOH/AcOH/H$_2$O 1:1:1:1). The rotary power is $(\alpha)^{25°\ C.}$ (546 nm) = −25.8° (c 0.2; H$_2$O). Analysis by NMR $^1$H gives the following results: (D$_2$O): 7.8–7.3, m, 3H (ArH$^1$H$^2$H$^3$); 7.60, m, 5H (C$_6$H$_5$S+); 5.13, m, 2H (ArCH$_2$S+); 4.26, m, 1H (CHαLys); 3.94, m, 8H (4 CH$_2$ Gly); 3.29, s, 3H (CH$_3$S+); 2.96, m, 2H (CH$_2$ εLys); 1.9–1.4, m, 6H (CH$_2$βγδLys).

EXAMPLE 10

Preparation of the Cyclopeptide of Formula (XXIX)

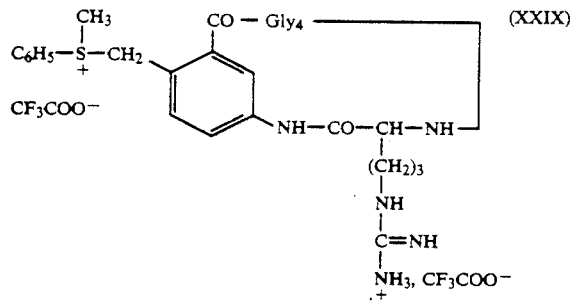

This formula corresponds to a cyclopeptide derivative of formula (I), in which R$^1$ represents C$_6$H$_5$+(CH$_3$)—, CF$_3$COO−; R$^2$ a hydrogen atom, Z represents CO(Gly)$_4$, R$^3$ represents NH and C(O)—AA is derived from arginine. An operating procedure similar to that of Example 1 (stages 1 to 6) and Example 9 is followed, except that in the third stage of Example 1, the compound of formula (XVIII) is reacted with arginine, whose αNH$_2$ group is protected by a butyloxycarbonyl group Boc. This gives the cyclopeptide of formula (XXIX), which has the following characteristics: Rf=0.14 (silica support; eluent EtOAc/nBuOH/AcOH/H$_2$O 1:1:1:1). The melting point is 125° to 130° C. (with decomposition). The rotary power is $(\alpha)^{25°\ C.}$ (546 nm) = −4° (c 0.1; H$_2$O). Analysis by nuclear magnetic resonance: $^1$H (D$_2$O): 7.8–7.3, m, 3H (ArH$^1$H$^2$H$^3$); 7.61, m, 5H (C$_6$H$_5$S+); 5.10, m, 2H (ArCH$_2$S+); 4.28, m, 1H (CHαArg); 3.95, m, 8H (4 CH$_2$ Gly); 3.30, s, 3H (CH$_3$S+); 3.20, m, 2H (CH$_2$δArg); 2.0–1.6, m, 4H (CH$_2$βγArg).

EXAMPLE 11

Preparation of the Cyclopeptide of Formula (XXIX')

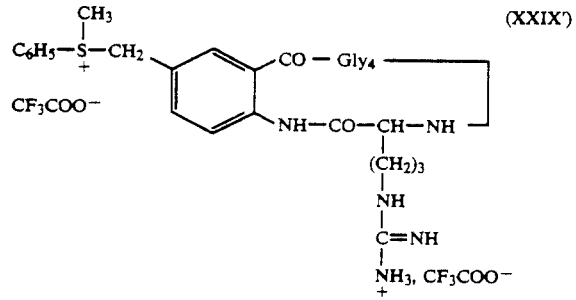

This compound is a position isomer of compound (XXIX). Its formula corresponds to a cyclopeptide derivative of formula (I), in which R$^1$ represents C$_6$H$_5$S+(CH$_3$)—, CF$_3$COO−, R$^2$ a hydrogen atom, Z represents CO(Gly)$_4$ in the ortho position (instead of the meta position) with respect to R$^3$, which represents NH and C(O)—AA is derived from arginine. An operating procedure similar to that of Example 10 is followed except that the arginine, whose αNH$_2$ group is protected by a Boc group, is coupled to the compound of formula (XVIII') obtained in the same way as (XVIII) from compound (II'), which is identical to (II) and which is itself obtained from 2-nitro-5-methyl-benzoic acid.

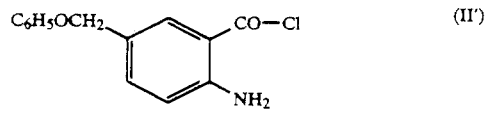

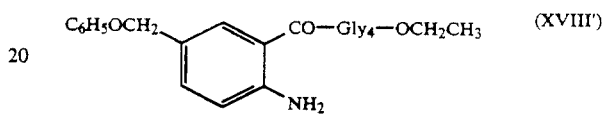

This gives the cyclopeptide of formula (XXIX'), which has the following characteristics: Rf=0.12 (silica support; eluent EtOAc/nBuOH/AcOH/H$_2$O 1:1:1:1). Melting point 140° to 150° C. (with decomposition). Rotary power $(\alpha)^{25°\ C.}$ (546 nm) = +7.37° (c 0.1; H$_2$O). Analysis by nuclear magnetic resonance: $^1$H (D$_2$O): 7.7–7.1, m, 8H (ArH$^1$H$^2$H$^3$ and C$_6$H$_5$S+); 4.60, m, 2H (ArCH$_2$S+); 4.30, m, 1H (CHαArg); 3.90, m, 8H (4 CH$_2$ Gly); 3.30, s, and 3.19, s, 3H (CH$_3$S+); 3.20, m, 2H (CH$_2$δArg); 2.1–1.5, m, 4H (CH$_2$βγArg).

EXAMPLE 12

Preparation of the Cyclopeptide of Formula (XXX)

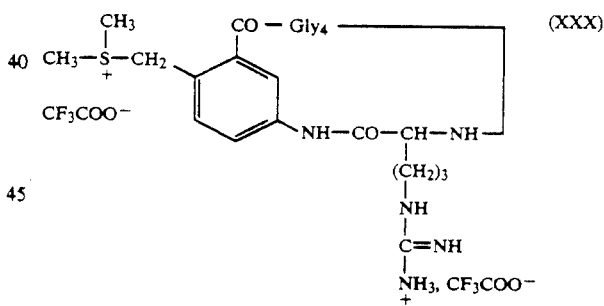

This formula corresponds to a cyclopeptide of formula (I), in which R$^1$ represents (CH$_3$)$_2$S+, CF$_3$COO−, R$^2$ a hydrogen atom, Z represents CO(Gly)$_4$, R$^3$ represents NH and C(O)—AA is derived from arginine. An operating procedure similar to that of Example 10 is followed, except that in the final stage the thioanisole is replaced by dimethyl sulphide. This gives the cyclopeptide of formula (XXX), which has the following characteristics: Rf=0.09 (silica support; eluent EtOAc/n-BuOH/AcOH/H$_2$O 1:1:1:1:1). Melting point 130° to 150° C. (with decomposition). Rotary power $(\alpha)^{25°\ C.}$ (546 nm) = −25.7° (c 0.25; H$_2$O). Analysis by nuclear magnetic resonance $^1$H (D$_2$O): 7.75, dd (J=2.1 Hz and 8.3 Hz), 1H (ArH$^2$); 7.63, d (J=2.1 Hz), 1H (ArH$^1$); 7.54, d (J=8.3 Hz), 1H (ArH$^3$); 4.68, s, 2H (ArCH$_2$S+); 4.27, m, 1H (CH αArg); 4.2–3.8, m, 8H (4 CH$_2$ Gly); 3.19, t (J=6.6 Hz), 2H (CH$_2$ δArg); 2.80, s, 6H ([CH$_3$]$_2$S+); 2.0–1.5, m, 4H (CH$_2$ βγArg).

EXAMPLE 13

Preparation of the Cyclopeptide of Formula (XXXI):

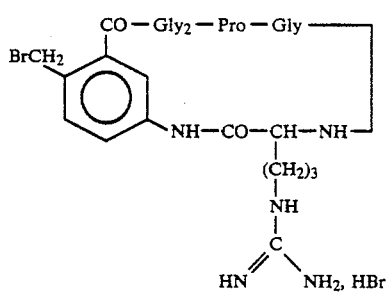
(XXXI)

This formula corresponds to a cyclopeptide derivative of formula (I), in which $R^1$ represents bromine, $R^2$ represents H, Z represents CO-Gly$_2$-Pro-Gly, $R^3$ represents NH and CO-AA is derived from arginine.

The operating procedure is identical to that of Example 3, except that in the second stage the compound of formula (II) is reacted with the compound H-Gly$_2$-Pro-Gly OC$_2$H$_5$ to obtain the compound of formula:

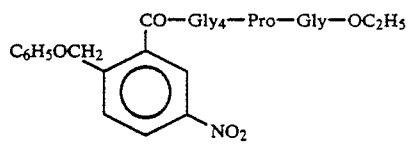

At the end of the final stage, the cyclopeptide of formula (XXXI) is obtained.

The rotary power is $[\alpha]_{546\ nm}^{25°\ C.} = -31.1$ (c 0.54; H$_2$O).

Analysis by NMR $^1$H gives the following results: (D$_2$O): 7.54, d, (J=1.6 Hz), 1H (ArH$_1$); 7.51, d (J=8 Hz), 1H (ArH$_3$); 7.48, dd (J=8 Hz and 1.6 Hz), 1H (ArH$_2$); 4.65, s, 2H (CH$_2$Br).

EXAMPLE 14

The inactivating or inhibiting properties of the functionalized cyclopeptides of formulas XXVIII, XXIX, XXIX', XXX and XXXI of Examples 9 to 13, summarized in Table 2 were tested with respect to a certain number of enzymes: bovine trypsin, human urokinase, human t-PA, human plasmin and porcine pancreatic elastase. The kinetic measurements were carried out at 25° C. in the following buffers: 0.1M Tris, 0.01M CaCl$_2$, pH 7.2 (bovine trypsin); 0.025M sodium phosphate, 0.1M NaCl, 0.05% (v/v) Tween 80, pH 7.5 (human urokinase); 0.05M Tris, 0.038M NaCl, 0.01% (v/v) Tween 80, pH 8.3 (human t-PA), 0.1M Tris (porcine pancreatic elastase), 0.1M sodium phosphate, 25% (v/v) glycerol (human plasmin). By using either the method of Hart and O'Brien, designated a (Biochemistry, 1973, Vol. 12, pp. 2940–2945) and/or that of Kitz and Wilson, designated by (J. Biol. Chem., 1962, Vol. 237, 32, pp. 3245–3249), the first order constant $k_i$ was determined which characterizes the infinite substrate concentration inactivation and the dissociation constant $K_i$ of the enzyme-inhibitor complex. Their ratio $k_i/K_i$ is an apparent second order constant characterizing the effectiveness of the inactivator. The results obtained are given in Table 2.

On the basis of the results of Tables 1 and 2, it can be seen that the cyclopeptide derivatives of Examples 9 to 13 are better inhibitors than the corresponding bromides of formulas XVI and XXIII of Examples 1 and 3.

Moreover, the cyclopeptide derivatives of Examples 9 to 12 are more stable in aqueous solution than the bromo derivatives of Examples 1 and 3.

Thus, the cyclopeptide derivatives according to the invention are selective inhibitors of certain proteases and can be used as the active substance in pharmaceutical compositions, which can be used in therapeutical applications in the pathologies referred to hereinbefore.

TABLE 1

Kinetic parameters characterizing the inactivation of serine proteases by functionalized cyclopeptides (25° C.).

| Cyclopeptide | Enzyme | $k_i/K_i$ (M$^{-1}$s$^{-1}$) |
|---|---|---|
| Compound (XXV) of Example 7 | Bovine chymotrypsin | 2.8 |
| Compound (XXIV) of Example 5 | Bovine chymotrypsin | 7 |
| Compound (XVI) of Example 1 | Bovine trypsin | 53 |
| | Human urokinase | 4.2 |
| Compound (XXIII) of Example 3 | Bovine trypsin | 150 |
| | Human urokinase | 165 |
| | Human t-PA | 0.3 |

TABLE 2

Kinetic parameters characterizing the inactivation of serine proteases by functionalized cyclopeptides (25° C.).

| Cyclopeptide | Enzyme 1) | $k_i/K_i$ (M$^{-1}$s$^{-1}$) | Method 2) |
|---|---|---|---|
| Derivative (XXVIII) of Example 9 | Trypsin | 490 | a |
| | Urokinase | 145 | b |
| | Plasmin | 53 | b |
| | Elastase | 0 | |
| Derivative (XXIX) of Example 10 | Trypsin | 824 | a |
| | Urokinase | 1967 | a and b |
| | t-PA | 1.4 | b |
| | Elastase | 0 | b |
| Derivative (XXIX') of Example 11 | Trypsin | 16.7 | a |
| | Urokinase | 14 | a |
| | Elastase | 0 | b |
| Derivative (XXX) of Example 12 | Trypsin | 7 | b |
| | Urokinase | 108 | b |
| | Elastase | 0 | b |
| | t-PA | 0 | b |
| Derivative (XXXI) of Example 13 | Trypsin | 2016 | a |

1) Enzymes:
Trypsin: bovine trypsin
Urokinase: human urokinase
t-PA: tissue activator of human plasminogen
Plasmin: human plasmin
Elastase: porcine pancreatic elastase
2) Methods
a: Hart and O'Brien method.
b: Kitz and Wilson method.

We claim:

1. Cyclopeptide derivative usable as a protease inhibitor, characterized in that it complies with the formula:

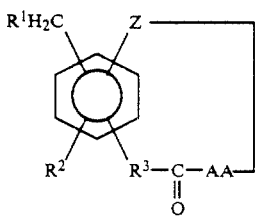 (I)

in which:

R¹ is chosen from among chlorine, fluorine, bromine and iodine atoms and the radicals $OSO_2R^4$, $OP(O)R^4_2$, $OC(O)R^4$ and $S^+R^4_2X_{1/v}^{v-}$ with $R^4$ representing an alkyl, perfluoroalkyl or aryl radical, in which the $R^4$ can be different and $X^-$ represents an anion of valency v;

R² is a hydrogen atom, an alkyl radical, a halogen atom, $NO_2$, $COOR^5$, $CF_3$ CN or $SO_2R^5$ with $R^5$ representing an alkyl or aryl radical;

R³ stands for an oxygen atom, a sulphur atom or —NH—;

Z comprises a peptide sequence $Z_1$ of amino acids or identical or different analogs and a group chosen from among $-(CH_2)_n$, $-O(CH_2)_n-$ or CO— at its end connected to the aromatic nucleus with n being an integer from 1 to 8;

a radical derived from an amino acid or an amino acid analog of formula:

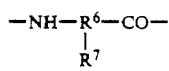

in which $R^6$ represents —N— or —CH— and $R^7$ represents a radical chosen from among H, $-CH_3$, $-CH_2CH(CH_3)_2$;

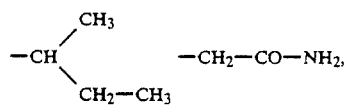

$CH_2-CH_2-COOH$, $-CH_2-CH_2-CO-NH_2$—$(CH_2)_4-NH_2$, $-CH_2OH$, $-CH_2-SH$

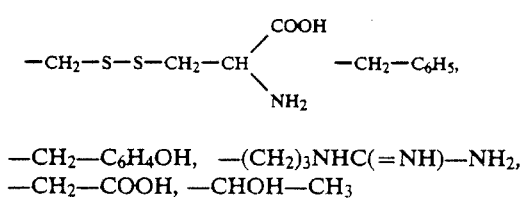

$-CH_2-C_6H_4OH$, $-(CH_2)_3NHC(=NH)-NH_2$,
$-CH_2-COOH$, $-CHOH-CH_3$

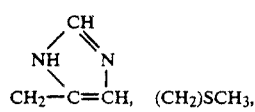

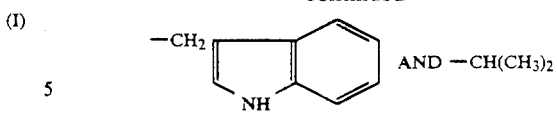

or of formula:

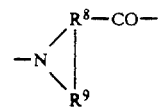

in which $R^8$ represents N or CH and $R^9$ represents the radical $-(CH_2)_3-$ or $-CH_2-CHOH-CH_2$, as well as its addition salts to a pharmaceutically acceptable acid.

2. Cyclopeptide derivative according to claim 1, characterized in that the peptide sequence $Z_1$ comprises 2 to 8 amino acids or amino acid analogs, which can be the same or different.

3. Cyclopeptide derivative according to one of the claims 1 or 2, characterized in that $R^3$ is in the ortho or meta position with respect to Z and in the ortho or para position with respect to $R^1H_2C$.

4. Cyclopeptide derivative according to claim 1 usable as a trypsin inhibitor, characterized in that —AA—C—(O)— complies with the formula:

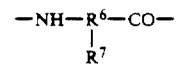

in which $R^6$ is CH and $R^7$ is $-(CH_2)_4NH_2$ or $-(CH_2)_3$ NH—C(=NH)—$NH_2$.

5. Cyclopeptide derivative according to claim 4, characterized in that $R^1$ is Cl, Br or $OSO_2R^4$.

6. Cyclopeptide derivative according to claim 1, characterized in that $R^1$ represents $S^+R^4_2X_{1/v}^{v-}$.

7. Cyclopeptide derivative according to claim 6, characterized in that $R^1$ represents

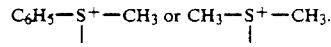

8. Cyclopeptide derivative according claim 4, characterized in that $R^2$ is a hydrogen atom.

9. Cyclopeptide derivative according to claim 2, characterized in that Z complies with the formula:

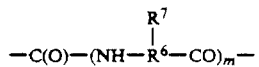

with m=4, 5 or 6 and $R^6$ and $R^7$ having the meanings given in claim 1.

10. Pharmaceutical composition having the property of inhibiting a given protease, characterized in that it comprises a pharmaceuticaly acceptable quantity of a cyclopeptide derivative according to claim 1.

11. Composition according to claim 10, characterized in that the protease belongs to the group comprising trypsin, chymotrypsin, elastase or active cysteine proteases.

12. Cyclopeptide derivative according to claim 2 wherein the peptide sequence $Z_1$ comprises 4 aminoacids consisting of glycine.

* * * * *